United States Patent [19]

Marchionna et al.

[11] Patent Number: 5,238,895
[45] Date of Patent: Aug. 24, 1993

[54] CATALYST SYSTEM AND PROCESS FOR THE LIQUID-PHASE PRODUCTION OF METHANOL FROM SYNTHESIS GAS

[75] Inventors: Mario Marchionna; Massimo Lami, both of Milan, Italy

[73] Assignee: Eniricerche S.p.A. and Snamprogetti S.p.A., Milan, Italy

[21] Appl. No.: 851,325

[22] Filed: Mar. 16, 1992

[30] Foreign Application Priority Data

Mar. 22, 1991 [IT] Italy .................. MI91 A 000775

[51] Int. Cl.$^5$ ............................................. B01J 31/00
[52] U.S. Cl. ..................................... 502/169; 502/171
[58] Field of Search ................................ 502/169, 171

[56] References Cited

U.S. PATENT DOCUMENTS 3,966,782 6/1976 Cipriani et al. ..................... 502/155
4,731,386 3/1988 Onsager .............................. 502/171

FOREIGN PATENT DOCUMENTS 0363802 4/1990 European Pat. Off. .
0375071 6/1990 European Pat. Off. .

Primary Examiner—Patrick P. Garvin
Assistant Examiner—Brent M. Peebles
Attorney, Agent, or Firm—Shea & Gould

[57] ABSTRACT

A catalyst system for the liquid-phase production of methanol from synthesis gas is described, consisting of:
one or more copper compounds;
one or more alkoxides of the lanthanum group of formula $(R_1O)_xLn$ and/or one or more inorganic oxides of the lanthanum and/or aluminum group;
one or more alkaline and/or alkaline-earth alkoxides of formula $(R_aO)_xM$,
if at least one alkoxide of the lanthanum group is present, then one or more alkoxides of the titanium group of formula $(R_tO)_xT$,
where $R_1$, $R_a$ and $R_t$, which can be the same or different, are $C_1$–$C_{10}$ alkyl groups,
M is the alkaline or alkaline-earth metal,
Ln is an element of the lanthanum group,
T is an element of the titanium group,
x is equal to the valency of the metal or element.

7 Claims, No Drawings

CATALYST SYSTEM AND PROCESS FOR THE LIQUID-PHASE PRODUCTION OF METHANOL FROM SYNTHESIS GAS

This invention relates to a catalyst system and process for the liquid-phase production of methanol from synthesis gas. Methanol or methyl alcohol, produced industrially for many decades, has always been valued for its use as an intermediate in the chemical industry.

Its characteristic of burning without emitting pollutant substances such as $NO_x$, $SO_x$ and dust when used in steam generators or gas turbines, and its property of considerably reducing CO emission when used in mixture with gasoline, make methyl alcohol an ecological energy carrier.

Its use as an energy carrier also has a strategic component in that it enables marginal natural gas reserves to be utilized which would be otherwise unusable.

All the industrial methods for producing methanol are very similar to each other and are based on two fundamental stages, namely a first stage in which the raw material is converted into synthesis gas and a second stage in which the $CO/H_2/CO_2$ mixture is converted into methyl alcohol with heterogeneous gaseous phase catalysis. The industrial operating conditions for latest generation copper catalysts are a pressure of 5–10 MPa, a temperature of 230°–270° C. and an $H_2$–$CO_2$/$CO+CO_2$ make-up gas composition of 5/1–8/1 (by volume).

The relatively low conversion per pass and the consequent need to maintain a low synthesis gas inerts content is the main limitation of current technology.

Catalyst systems operating under very mild temperature and pressure conditions (90°–120° C. and 1–5 MPa respectively) have recently been developed. With these it is possible to obtain a very high CO conversion of greater than 90% per pass, to thus well overcome the main limitations of current technology.

Many of these systems use nickel as the catalyst metal. Some operate in the form of slurry (see the patents U.S. Pat. No. 4,614,749, U.S. Pat. No. 4,619,946, U.S. Pat. No. 4,623,634) while others use homogeneous catalysis (see patent applications EP-285228, EP-287151 and EP-289067 of SHELL).

all these systems have however the drawback of developing nickel carbonyl, a very toxic substance, under reaction conditions. Another system has been developed by MITSUI Petrochem. Ind. Ltd. and uses not nickel but copper catalysts (see Japanese patent applications JP-110631/81 and JP-128642/82).

The catalyst system of JP-128642/82 is characterised by the presence of copper compounds, preferably copper alkoxides, copper aryloxides, copper halides, copper carboxylates and copper hydrides together with alkaline metal alkoxides, preferably sodium methoxide.

Although this catalyst system shows interesting characteristics such as its capacity to produce methanol under very mild reaction conditions, it has the limitation of low productivity, this being a limitation from the applicational viewpoint.

In our previous investigations it has also been found that the said catalyst system for methanol production can operate with decidedly higher activity if specific additions of methanol and/or alkyl formate, preferably methyl formate, are made (see EP-375071 of SNAM-PROGETTI S.p.A.).

It has now been surprisingly found that the addition of one or more alkoxides of metals of the lanthanum group and/or the addition of one or more inorganic oxides of the lanthanum and/or aluminium group, possibly in the presence of one or more alkoxides of the titanium group if at least one alkoxide of the lanthanum group is present, provides a catalyst system which produces methanol with decidedly higher activity.

The promoter effect of lanthanides on CO hydrogenation systems has already been observed both in homogeneous catalysis with ruthenium systems (U.S. Pat. No. 4,590,216 of Union Carbide Corp.) and in heterogeneous catalysis (G. Owen et al., Appl. Catal., 33, 1987, 405) with Cu/Ln intermetal alloys where Ln is a generic element of the lanthanum group.

Both these systems operate under very different temperature and pressure conditions from those used by us in the process of the present invention.

The addition of titanium alkoxides has already been claimed, in patent application JP-128642/82, but in the present application it will be demonstrated that the titanium alkoxides exhibit their positive effect only in the presence of alkoxides of the lanthanum group.

The promoter effect of halides of metals of the lanthanum group has already been observed (final Report DE-AC 22-84PC70022 by Union Carbide Corp. to U.S. Department of Energy, January 1987), but as will be demonstrated hereinafter in the examples it is less effective than the addition of alkoxides or oxides, and in some cases can produce negative results because of catalyst poisoning by chlorine.

The promoter effect of adding inorganic oxides of the lanthanum or aluminium group has never been described on systems of this type. It should be noted that replacing part of the alkaline (or alkaline earth) alkoxide by an alkoxide of the lanthanum group (alone or in the presence of an alkoxide of the titanium group) results in higher activity, while maintaining the $RO^-$/Cu ratio fixed where the alkoxide ion $RO^-$ is bonded in accordance with correct stoichiometry to a metal Z to give a compound $(RO)_xZ$, where Z is an alkaline or alkaline-earth metal of the lanthanum or titanium group. However, the catalyst system does not work if the alkaline (or alkaline-earth) metal alkoxide is totally excluded.

The joint presence of alkoxides of the lanthanum group with alkoxides of the titanium group results in a system which is as active as that using only alkoxides of the lanthanum group but is decidedly less costly because of the smaller quantities of lanthanum group derivatives used.

The addition of inorganic oxides to the system described in EP-375071 also leads to a decidedly more active system.

The addition of methanol and/or alkyl formate also favours decidedly higher productivity in the present invention, although operating under very mild reaction conditions.

The quantity of methanol and/or alkyl formate added is strictly related to the reaction parameters such as the copper composition, alkoxide concentration and operating pressure and temperature.

As the reaction conditions and catalyst composition vary, the optimum quantity of methanol and/or alkyl formate to be added also varies, as illustrated in EP-375071.

However negative effects can be obtained if the methanol and/or alkyl formate quantities added are outside the range we have indicated hereinafter.

A further and very important consequence of this surprising discovery is that on passing from a batch system to a continuous system, the useful methanol fraction has to be recycled for the system to operate under best conditions.

The catalyst system of the present invention for the liquid-phase production of methanol from synthesis gas is characterised by consisting of:

one or more copper compounds;

one or more alkoxides of the lanthanum group of formula $(R_1O)_xLn$ and/or one or more inorganic oxides of the lanthanum and/or aluminium group;

one or more alkaline and/or alkaline-earth alkoxides of formula $(R_aO)_xM$, if at least one alkoxide of the lanthanum group is present, then one or more alkoxides of the titanium group of formula $(R_tO)_xT$, where $R_1$, $R_a$ and $R_t$, which can be the same or different, are $C_1$–$C_{10}$ alkyl and preferably $C_1$–$C_5$ alkyl groups, M is the alkaline or alkaline-earth metal, Ln is an element of the lanthanum group, T is an element of the titanium group, x is equal to the valency of the metal or element, the $(R_aO)_xM/Cu$ molar ratio being equal to or greater than 4, the $(R_1O)_xLn+(R_tO)_xT/(R_aO)_xM$ molar ratio being between 0.01 and 0.3 if at least one alkoxide of the lanthanum group is present, and the inorganic oxide/Cu molar ratio being greater than 0.5 if at least one inorganic oxide of the lanthanum or aluminium group is present.

Elements of the lanthanum group are meant those with an atomic number of between 57 and 71, but also including scandium and yttrium.

Elements of the titanium group are meant titanium, zirconium and hafnium.

The catalyst can be prepared by mixing the copper compound with the alkoxides (and with the oxides), preferably in an organic diluent which is liquid under the reaction conditions.

Copper compounds usable in the present invention include by way of example copper carboxylates such as copper acetate, copper halides such as copper chloride or bromide, copper alkoxides such as copper (I) or (II) methoxide, and copper hydride.

The inorganic oxides are firstly dried by calcining and are then added as such to the reaction mixture.

A preferred form of said catalyst system consists of:

copper (I) chloride, sodium methoxide ($CH_3ONa$), samarium (or lanthanum) methoxide (in the presence or absence of titanium methoxide) or cerium (or samarium) oxide.

The process for the liquid-phase production of methanol from synthesis gas, to which the present invention also relates, is characterised by reacting CO with $H_2$ in the presence of the aforedescribed catalyst system and of one or more solvents, to which are added methanol and/or one or more alkyl formates of formula $HCOOR_f$, where $R_f$ is a $C_1$–$C_{20}$ alkyl and preferably a $C_1$–$C_{10}$ alkyl and more preferably a $C_1$ alkyl group in a quantity such as to obtain, in the case of methanol addition, a methanol/Cu molar ratio of between 1 and 500 and preferably between 3 and 30, or in the case of alkyl formate addition, a $HCOOR_f/Cu$ molar ratio of between 1 and 1000 and preferably between 4 and 400, operating at a temperature higher than 40° C. and lower than 200° C. and preferably between 60° and 150° C., and with a copper concentration in the solution formed from the solvents and catalyst system of between 0.001 and 1 molar and preferably between 0.01 and 0.09 molar.

The partial pressure of the reagents is preferably greater than 1 MPa and more preferably between 3 and 7 MPa.

The $H_2/CO$ molar ratio of the reacting gases is preferably between 0.5 and 5 and more preferably between 1.5 and 3.5.

The aforedescribed catalyst system can operate in a solvent of simple ether type (such as methyltertbutylether, tetrahydrofuran, normalbutylether, anisole, veratrol), of complex ether type (glycolethers such as diglyme or tetraglyme), or of carboxylic acid ester type (such as methyl isobutyrate or $\gamma$ butyrolactone). Other usable solvents include sulphones (such as tetramethylenesulphone), sulphoxides (such as dimethylsulphoxide) or amines (such as pyridine, piperidine or picoline).

The system can also operate with high percentages (such as 30–60% by volume) of inerts such as $N_2$ and $CH_4$ in the reaction gas without altering the reaction rate, provided the partial pressure of the reactants is kept higher than 1 MPa.

This aspect is very important because it provides a different and more economical method for preparing synthesis gas such as partial oxidation with air.

Operating under the indicated preferred conditions, maximum CO conversions per pass of the order of 90% have been obtained, with a reaction rate of about $0.06s^{-1}$ (moles of $CH_3OH$ developed per mole of copper per second) and with high methanol selectivity (up to 99%), the only notable by-products being dimethylether and methyl formate.

Some examples are given below for the purpose of illustrating the invention, but without in any way representing a limitation thereon.

EXAMPLE 1

This example illustrates the use of the process of the present invention in a batch reactor at 90° C. and 5 MPa.

3 mmoles of CuCl, 51 mmoles of $CH_3ONa$, 3 mmoles of $Sm(OMe)_3$, 15 mmoles of methanol and 90 ml of anhydrous tetrahydrofuran are mixed in a 300 ml pressure vessel with magnetic stirring. The operation is conducted in a nitrogen atmosphere.

The alkoxides of the lanthanum group metals can be easily prepared from $CH_3OLi$ and the chloride of the lanthanum group metal, by the procedure described in the literature ["Metal Alkoxides", D. C. Bradley, R. C. Mehrotra, D. P. Gaur eds., Academic Press, London (1978) and the references contained therein].

The reactor is loaded to 1 MPa with a $CO/H_2$ mixture (½ molar), heated to 90° C. and the total pressure then raised to 5 MPa with the same mixture.

The pressure tends to reduce during the test because of the reaction. To compensate for this pressure reduction fresh make-up gas is continuously added to maintain the pressure constant at 5 MPa.

Operating in this manner, 710 mmoles of methanol (excluding the initial quantity), 144 mmoles of methyl formate and 1.60 mmoles of dimethylether are obtained after 7 hours of reaction.

EXAMPLE 2

The procedure of Example 1 is followed but using 3 mmoles of $La(OMe)_3$ instead of $Sm(OMe)_3$.

Operating in accordance with the procedure of Example 1, 590 mmoles of methanol (excluding the initial quantity), 114 mmoles of methyl formate and 1.62 mmoles of dimethylether are obtained after 7 hours of reaction.

EXAMPLE 3 (Comparative)

This example demonstrates that the absence of the lanthanum group alkoxide results in a less active catalyst system.

The operation is carried out under the same process conditions as Example 1, but without adding Sm(OMe)$_3$.

Operating in accordance with the procedure of Example 1, 455 mmoles of methanol (excluding the initial quantity), 95 mmoles of methyl formate and 2.58 mmoles of dimethylether are obtained after 7 hours of reaction.

EXAMPLE 4 (Comparative)

This example demonstrates that if the lanthanum group methoxide is replaced with the same molar quantity of alkoxide ion present in MeONa, a less active system is still obtained.

The same process conditions as Example 1 are used but with 60 mmoles of MeONa and without the Sm(OMe)$_3$.

Operating in accordance with the procedure of Example 1, 506 mmoles of methanol (excluding the initial quantity), 113 mmoles of methyl formate and 3.90 mmoles of dimethylether are obtained after 7 hours of reaction.

EXAMPLE 5

This example demonstrates that the promoter effect of the lanthanum group alkoxides persists even at lower MeO$^-$/Cu ratios. 21 mmoles of MeONa and 3 mmoles of Sm(OMe)$_3$ are fed, the other conditions being as given in Example 1.

Operating in accordance with the procedure of Example 1, 382 mmoles of methanol (excluding the initial quantity), 114 mmoles of methyl formate and 0.31 mmoles of dimethylether are obtained after 7 hours of reaction.

EXAMPLE 6 (Comparative)

This example demonstrates that adding a halide of the lanthanum group metal results in a system which is much less active than that comprising an alkoxide of the same group.

The same process conditions as Example 5 are used, but feeding 30 mmoles of MeONa and 3 mmoles of SmCl$_3$.

Operating in accordance with the procedure of Example 1, 56 mmoles of methanol (excluding the initial quantity), and 14 mmoles of methyl formate are obtained after 7 hours of reaction.

EXAMPLE 7 (Comparative)

This example demonstrates that even operating at lower MeO$^-$/Cu ratios, replacing the alkoxide of the lanthanum group metal with MeONa results in a less active system.

The same process conditions as Example 5 are used, but without adding Sm(OMe)$_3$, and using 30 mmoles of MeONa.

Operating in accordance with the procedure of Example 1, 336 mmoles of methanol (excluding the initial quantity), 89 mmoles of methyl formate and 0.37 mmoles of dimethylether are obtained after 7 hours of reaction.

EXAMPLE 8

The procedure of Example 5 is followed, but adding 3 mmoles of La(OMe)$_3$ instead of Sm(OMe)$_3$.

Operating in accordance with the procedure of Example 1, 361 mmoles of methanol (excluding the initial quantity), 87 mmoles of methyl formate and 0.15 mmoles of dimethylether are obtained after 7 hours of reaction.

EXAMPLE 9 (Comparative)

This example demonstrates that the system cannot operate in the absence of MeONa.

The same process conditions as Example 8 are used, but without MeONa and with 10 mmoles of La(OMe)$_3$.

Operating in accordance with the procedure of Example 1, 8 mmoles of methanol (excluding the initial quantity) and 3 mmoles of methyl formate are obtained after 7 hours of reaction.

EXAMPLE 10 (Comparative)

This example demonstrates that the addition of an alkoxide of the titanium group does not produce a promoter effect greater than an equal molar quantity of alkoxide in MeONa alone.

45 mmoles of MeONa and 3.75 mmoles of Ti(OMe)$_4$ are fed, the other conditions being those given in Example 1.

Operating in accordance with the procedure of Example 1, 430 mmoles of methanol (excluding the initial quantity), 101 mmoles of methyl formate and 1.01 mmoles of dimethylether are obtained after 7 hours of reaction.

This example should be compared with Example 4.

EXAMPLE 11

This example demonstrates that the addition of a small quantity of an alkoxide of the lanthanum group to the alkoxide of the titanium group results in a more active system than those of the comparable examples (Examples 4, 10).

1 mmoles of Sm(OMe)$_3$ and 3 mmoles of Ti(OMe)$_4$ are fed, the other conditions being as given in Example 1.

Operating in accordance with the procedure of Example 1, 621 mmoles of methanol (excluding the initial quantity), 172 mmoles of methyl formate and 1.69 mmoles of dimethylether are obtained after 7 hours of reaction.

EXAMPLE 12

This example demonstrates that the presence of the titanium group alkoxide is advisable to obtain an active system when the lanthanum group alkoxide is used.

The operating conditions are those of Example 11, but without using Ti(OMe)$_4$.

Operating in accordance with the procedure of Example 1, 520 mmoles of methanol (excluding the initial quantity), 120 mmoles of methyl formate and 1.99 mmoles of dimethylether are obtained after 7 hours of reaction.

EXAMPLE 13

The same process conditions as Example 11 are used, but feeding 1 mmoles of La(OMe)$_3$ instead of Sm(OMe)$_3$.

Operating in accordance with the procedure of Example 1, 537 mmoles of methanol (excluding the initial quantity), 137 mmoles of methyl formate and 1.20 mmoles of dimethylether are obtained after 7 hours of reaction.

The following examples demonstrate that the addition of inorganic oxides has a promoter effect greater than the system used in Example 4, and corresponding to that claimed in EP-375071.

EXAMPLE 14

The same process conditions as Example 4 are used, adding 2.5 g of Al$_2$O$_3$.

Operating in accordance with the procedure of Example 1, 594 mmoles of methanol (excluding the initial quantity), 92 mmoles of methyl formate and 1.16 mmoles of dimethylether are obtained after 7 hours of reaction.

EXAMPLE 15

The same process conditions as Example 4 are used, adding 5 g of CeO$_2$.

Operating in accordance with the procedure of Example 1, 780 mmoles of methanol (excluding the initial quantity), 108 mmoles of methyl formate and 2.35 mmoles of dimethylether are obtained after 7 hours of reaction.

EXAMPLE 16

The same process conditions as Example 4 are used, adding 5 g of La$_2$O$_3$.

Operating in accordance with the procedure of Example 1, 656 mmoles of methanol (excluding the initial quantity), 119 mmoles of methyl formate and 2.31 mmoles of dimethylether are obtained after 7 hours of reaction.

EXAMPLE 17

The same process conditions as Example 4 are used, adding 5 g of Sm$_2$O$_3$.

Operating in accordance with the procedure of Example 1, 766 mmoles of methanol (excluding the initial quantity), 90 mmoles of methyl formate and 1.86 mmoles of dimethylether are obtained after 7 hours of reaction.

We claim:

1. A catalyst system for the liquid-phase production of methanol from synthesis gas, characterised by consisting of:
   one or more copper compounds selected from the group consisting of copper carboxylates, copper halides, copper alkoxides, copper hydrides, and copper aryloxides;
   one or more alkoxides of the lanthanum group of formula $(R_1O)_x$Ln and/or one or more inorganic oxides of the lanthanum and/or aluminum group;
   one or more alkaline and/or alkaline-earth alkoxides of formula $(R_aO)_x$M,
   if at least one alkoxide of the lanthanum group is present, then one or more alkoxides of the titanium group of formula $(R_tO)_x$T,
   where $R_1$, $R_a$ and $R_t$, which can be the same or different, are $C_1$–$C_{10}$ alkyl groups, M is the alkaline or alkaline-earth metal, Ln is an element of the lanthanum group, T is an element of the titanium group, x is equal to the valency of the metal or element, the $(R_aO)_x$M/Cu molar ratio being equal to or greater than 4, the $R_1O)_x$Ln+$(R_tO)_x$T/$(R_aO)_x$M molar ratio being between 0.01 to 0.3 if at least one alkoxide of the lanthanum group is present, and the inorganic oxide/Cu molar ratio being greater than 0.5 if at least one inorganic oxide of the lanthanum or aluminum group is present.

2. A catalyst system as claimed in claim 1, wherein $R_1$, $R_a$ and $R_t$, which can be the same or different, are $C_1$–$C_5$ alkyl groups.

3. A catalyst system as claimed in claim 1, wherein the element of the lanthanum group has an atomic number of between 57 and 71, or is scandium or yttrium.

4. A catalyst system as claimed in claim 1, wherein the element of the titanium group is chosen from titanium, zirconium and hafnium.

5. A catalyst system as claimed in claim 1, wherein the copper compound is copper (I) chloride, the alkaline alkoxide is sodium methoxide, and the inorganic oxide of the lanthanum group is cerium oxide or samarium oxide.

6. A catalyst system as claimed in claim 1, wherein the copper compound is copper (I) chloride, the alkaline alkoxide is sodium methoxide, and the alkoxide of the lanthanum group is samarium or lanthanum methoxide.

7. A catalyst system as claimed in claim 6, wherein titanium methoxide is present as the alkoxide of the titanium group.

* * * * *